(12) United States Patent
Wang et al.

(10) Patent No.: US 7,547,798 B2
(45) Date of Patent: Jun. 16, 2009

(54) PROCESS FOR PREPARING AMINOBENZOATE ESTERS

(75) Inventors: Andrew Wilson Wang, Macungie, PA (US); George Ernest Grossmann, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 11/829,418

(22) Filed: Jul. 27, 2007

(65) Prior Publication Data

US 2009/0030226 A1    Jan. 29, 2009

(51) Int. Cl.
*C07C 229/00* (2006.01)
(52) U.S. Cl. ........................................ 560/50
(58) Field of Classification Search ........ None
See application file for complete search history.

(56) References Cited

U.S. PATENT DOCUMENTS

| | | | |
|---|---|---|---|
| 2,714,607 A * | 8/1955 | Matter | 560/50 |
| 4,732,959 A | 3/1988 | Otani et al. | |
| 4,778,920 A * | 10/1988 | Kaufhold | 560/124 |
| 5,792,800 A | 8/1998 | Wideman et al. | |
| 6,020,392 A | 2/2000 | Kushner et al. | |
| 6,111,129 A | 8/2000 | Barrows et al. | |

FOREIGN PATENT DOCUMENTS

| | | |
|---|---|---|
| JP | 07-233130 A | 9/1995 |
| JP | 2000-351755 A | 12/2000 |
| WO | 00/29368 A | 5/2000 |

OTHER PUBLICATIONS

M.G. Abdullaev, Development of the Method of Novocain Production, Pharma. Chem. Jour., vol. 35, No. 10, 2001, pp. 556-559.

* cited by examiner

*Primary Examiner*—Paul A Zucker
(74) *Attorney, Agent, or Firm*—Rosaleen P. Morris-Oskanian

(57) ABSTRACT

The present invention herein provides a process for making an aminobenzoate ester of an alcoholic organic compound. In one aspect, there is provided a process for making an aminobenzoate ester comprising the steps of: (a) providing a reaction mixture comprising an alkyl aminobenzoate, an alcohol reagent and a suitable transesterification catalyst; (b) introducing an auxiliary alcohol to the reaction mixture; and (c) exposing the reaction mixture to conditions effective to provide an end-product mixture comprising the aminobenzoate ester.

17 Claims, 2 Drawing Sheets

PROCESS FOR PREPARING AMINOBENZOATE ESTERS

BACKGROUND OF THE INVENTION

The present invention relates generally to processes for preparing aminobenzoate esters. More particularly, the present invention relates generally to a process for the preparation of an aminobenzoate ester of an alcoholic organic compound containing one or more hydroxyl groups. In certain embodiments, the alcoholic organic compound has an oligomeric or polymeric backbone having from 2 to 300 repeating units.

Aminobenzoate esters are useful as oligomeric amine curatives in a wide variety of applications such as, but not limited to, coatings, adhesives, castable elastomers, molded products, and tougheners or flexibilizers for epoxy-based materials. The reaction to produce these organic esters is typically a transesterification reaction such as that depicted in Equation 1 wherein an alkyl aminobenzoate (1) reacts with an alcohol reagent (2) in the presence of a catalyst (not shown) to form the aminobenzoate ester (3) and the corresponding byproduct alkyl alcohol (4). This reaction is typically an equilibrium reaction that proceeds nearly to completion if an excess of one reactant is used and the product is removed from the reaction mixture such as by, for example, distillation or fractionation.

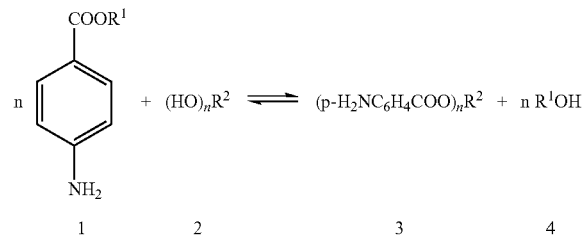

Equation 1

One alkyl aminobenzoate that can be used to produce the aminobenzoate ester is ethyl 4-aminobenzoate, also known as benzocaine. However, the relatively high vapor pressure of ethyl 4-aminobenzoate may cause it to be lost from the reaction mixture thereby resulting in a reduction in yield of aminobenzoate ester end-product as well as the deposition of solid ethyl 4-aminobenzoate in the reaction equipment. As a result, the typical industry practice is to use a less volatile reagent such as butyl 4-aminobenzoate, also known as butamben, which can be added to the reaction mixture separately or formed in the reaction mixture in situ. The use of butyl 4-aminobenzoate to produce the aminobenzoate ester has some drawbacks. At the present time, butyl 4-aminobenzoate is a less economical reagent than ethyl 4-aminobenzoate. Further, the reaction of butyl 4-aminobenzoate with the alcohol reagent is considerably slower than that of ethyl 4-aminobenzoate.

Yet another solution to prevent the loss of ethyl 4-aminobenzoate from the reaction mixture may be to introduce a hydrocarbon solvent such as, for example, toluene or xylene, into the reaction mixture. The hydrocarbon solvent provides a reflux thereby keeping the reagents within the reaction mixture and improving the reaction efficiency. However, this solution generally requires the additional step of removing these solvents from the end-product such as, for example, by stripping. Further, since many of these solvents present health hazards and because their chemical properties are quite different from the reagents, by-products, and products present in the reaction, it is generally necessary to remove them to very low levels to produce a commercially viable product.

Although preparation of aminobenzoate esters and other organic esters are known in the art, improved methods of making aminobenzoate esters are still sought by those skilled in the art. For example, U.S. Pat. No. 6,111,129 or the '129 patent teaches the production of alkanediol-diaminobenzoates which are useful as curing agents for the production of polyurethane ureas. The alkanediol-diamenzoates are prepared by a transesterification reaction of an alkyl-p-aminobenzoate with an unpolymerized diol—typically in a stoichiometric ratio of at least 2:1 or greater alkyl-p-aminobenzoate to diol—in the presence of a transesterification catalyst. The '129 patent discloses benzocaine as an alkyl-p-aminobenzoate that can be used in the reaction. The '129 patent further teaches the subsequent purification of the alkanediol-diaminobenzoate product by crystallization using an alcohol.

Similarly, U.S. Pat. No. 4,732,959 or the '959 patent teaches the preparation of poly(urethane)ureamides by reaction of a polyisocyanate and a p-aminobenzoate derivative of a polyester polyol. This latter derivative is prepared by transesterifying a polyesterpolyol with an aminobenzoic acid alkyl ester. Example 1 of the '959 patent teaches the transesterification reaction of a lactone-type polyesterpolyol with ethyl p-aminobenzoate or benzocaine and the removal of the byproduct of the reaction, or ethanol, as it was formed. Example 1 also teaches removing unreacted benzocaine from the reaction mixture by heating the mixture to 200° C. under vacuum for 3 hours to provide the polyesterpolyol derivative.

U.S. Pat. No. 5,792,800 or the '800 patent discusses the use of aminobenzoate esters as rubber-to-wire adhesion promoters. Example 1 of the '800 patent describes preparing octadecyl-4-aminobenzoate through the transesterification reaction of benzocaine with 1-octadecanol in a 1:1 stoichiometric ratio in a reaction mixture containing mixed xylenes.

The reference "Development of the Method of Novacain Production" by M. G. Abdullaev, Pharmaceutical Chemistry Journal, Vol. 35 No. 10 (2001), pp. 556-559 or "Abdullaev" teaches the synthesis of novocain using ethyl p-nitrobenzoate as a starting reagent by performing the hydrogenation and transesterification reactions simultaneously using a catalyst system that is active for both reactions. The simultaneous reactions are conducted at a relatively low temperature or around 45° C. Because of this relatively low temperature, the volatility of ethyl 4-aminobenzoate within the reaction mixture and deposition of solid ethyl 4-aminobenzoate in the reaction equipment may not be a concern.

Accordingly, there is a need for process for making aminobenzoate esters of an alcoholic organic compound using alkyl aminobenzoates without yield losses, slow reaction time, and/or operational problems associated with the volatility of the alkyl aminobenzoates.

BRIEF SUMMARY OF THE INVENTION

The present invention provides, in one aspect, a process that satisfies this need for improved methods for making an aminobenzoate ester of an alcoholic organic compound comprising the following formula (I) $(NH_2C_6H_5COO)_xR^2(OH)_y$, wherein $R^2$ is a linear or branched, substituted or unsubstituted alkyl and/or alkylene group comprising from 3 to 300 carbon atoms and wherein x and y are each independently a number ranging from 0 to 100 provided that neither x nor y are concurrently 0 where the process comprises the steps of: (a) providing a reaction mixture comprising an alkyl aminobenzoate comprising the following formula (II) $NH_2C_6H_4COOR^1$ where $R^1$ is an alkyl group comprising from 1 to 20 carbon atoms, an alcohol reagent comprising the following formula (III) $(HO)_nR^2$ wherein $R^2$ is a linear or branched, substituted or unsubstituted alkyl and/or alkylene group having from 3 to 300 carbon atoms and n is a sum of the expression "x+y", and an auxilliary alcohol wherein the auxiliary alcohol has a vapor pressure that is greater than a vapor pressure of the alkyl aminobenzoate and the aminobenzoate ester and (b) exposing the reaction mixture to conditions effective to provide an end-product mixture comprising the aminobenzoate ester.

In another aspect, there is provided a process for making an aminobenzoate ester comprising the steps of (a) providing a reaction mixture comprising an alkyl aminobenzoate and an alcohol reagent; (b) introducing an auxilliary alcohol to the reaction mixture wherein the auxiliary alcohol has a boiling point that is less than a boiling point of the alkyl aminobenzoate and a boiling point of the aminobenzoate ester; and (c) heating the reaction mixture to a temperature of 120° C. or greater for a time sufficient to produce an end-product mixture comprising the aminobenzoate ester. In one particular embodiment, step (b) is conducted during at least a portion of step (a).

In a further aspect, there is provided a process for making an aminobenzoate ester of comprising the steps of (a) providing a reaction mixture comprising an alkyl aminobenzoate and an alcohol reagent; (b) introducing an auxiliary alcohol to the reaction mixture wherein at least a portion of the auxiliary alcohol within the reaction mixture reacts to provide an alcohol by-product and wherein the alcohol by-product has a vapor pressure that is higher than a vapor pressure of the auxiliary alcohol; and (c) exposing the reaction mixture to conditions effective to provide an end-product mixture comprising the aminobenzoate ester. In certain embodiments, at least a portion of the auxiliary alcohol within the reaction mixture reacts to provide an alcohol by-product wherein the alcohol by-product has a vapor pressure that is higher than a vapor pressure of the auxiliary alcohol.

DETAILED DESCRIPTION OF THE INVENTION

Figure 1:
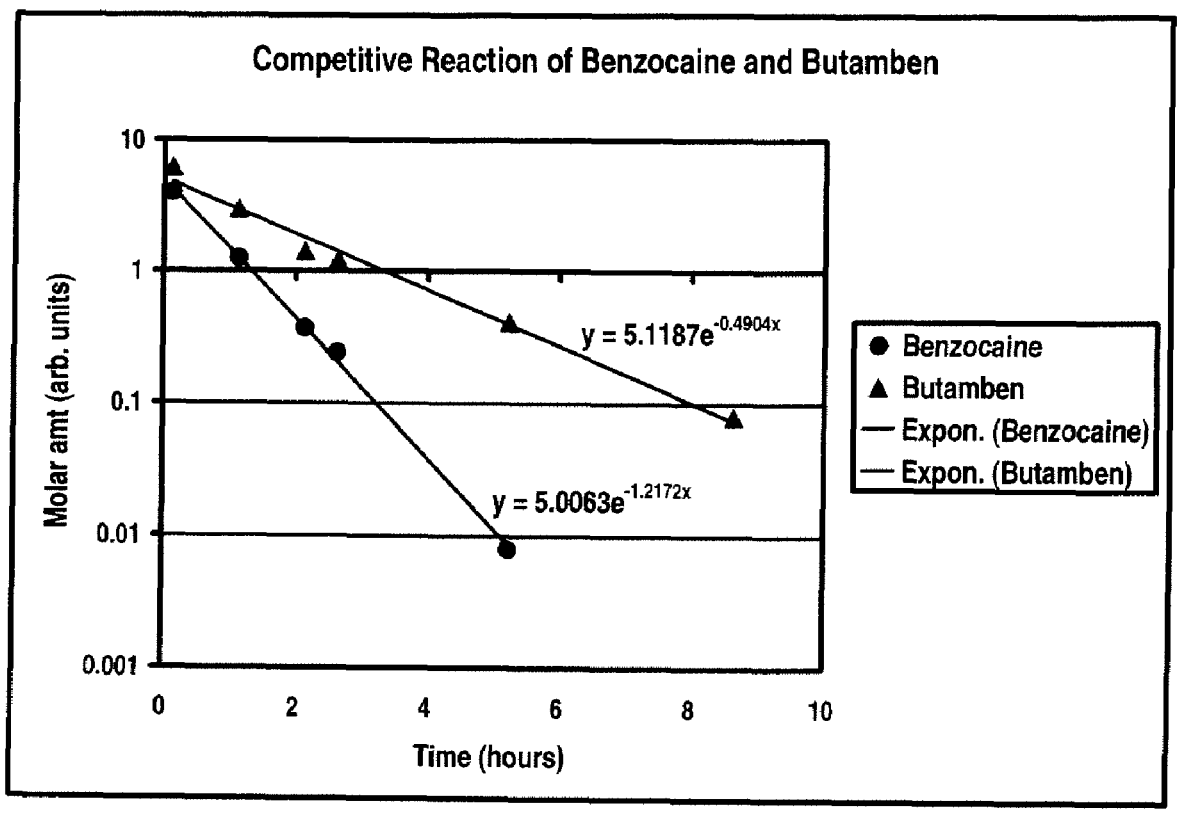
FIG. 1 compares the reaction rates of ethyl 4-aminobenzoate and butamben with poly(tetrahydrofuran) of the process described in Example 4.

The process described herein is an improved process for making an aminobenzoate ester of an alcoholic organic compound from an alkyl aminobenzoate that may avoid yield losses, slow reaction time, and/or operational problems due to the loss of the alkyl aminobenzoate reagent from the reaction mixture. The process described herein avoids these problems by introducing an auxilliary alcohol into the reaction mixture that has a boiling point that is less than the boiling point of the alkyl aminobenzoate and the boiling point of the aminobenzoate ester. The term "auxilliary alcohol" as used herein refers to an alcohol which reacts with the alkyl aminobenzoate reagent to form an alcohol by-product that is more volatile than itself and the alcohol reagent within the reaction mixture.

In one particular embodiment, the auxiliary alcohol that is added to the reaction mixture is 1-butanol and the alkyl aminobenzoate is ethyl 4-aminobenzoate. The 1-butanol auxiliary alcohol is more volatile than the ethyl 4-aminobenzoate and alcohol reagent within the reaction mixture thereby providing a reflux. While not being bound to theory, it is believed that this reflux prevents the ethyl 4-aminobenzoate from leaving the reaction mixture and forming solid deposits on overhead piping and equipment. Further, at least a portion of the 1-butanol reacts with ethyl 4-aminobenzoate to provide an alcohol by-product or ethanol. Since 1-butanol is less volatile than ethanol, ethanol can be selectively removed from the reaction mixture without significant loss of 1-butanol. In certain embodiments, once the majority of the ethanol by-product removal is complete, the 1-butanol can be removed.

The process described herein provides one or more or following advantages over other methodologies presently available. First, the process may permit the use of relatively lower cost reagents. For example, in certain embodiments, the process may use the reagent ethyl 4-aminobenzoate rather than the commonly used reagent butyl 4-aminobenzoate. At the present time, ethyl 4-aminobenzoate is more cost effective than butyl 4-aminobenzoate. Second, the process described herein may avoid the use of a hydrocarbon solvent such as toluene, xylene, benzene, hexane, or the like. Instead, in the process described herein, the by-product of the reaction of the alkyl benzoate and the auxilliary alcohol (such as ethanol which is a by-product of the reaction between ethyl 4-aminobenzoate and the auxilliary alcohol 1-butanol) are more easily removed from the end product mixture and/or are not as detrimental impurities within the end product mixture. It is believed that the auxilliary alcohol provides a reflux within the reactive mixture during the reaction and—unlike hydrocarbon solvents—further reacts with the alkyl aminobenzoate thereby reducing the amount of alkyl aminobenzoate present within the reaction mixture. In certain embodiments, the auxilliary alcohol itself and the alcohol by-product produced by reaction of the auxilliary alcohol with the alkyl aminobenzoate can be easily removed from the reaction mixture using distillation, fractionation, stripping, or other means. The process described herein also reduces the risk of loss of alkyl aminobenzoate such as ethyl 4-aminobenzoate from the reactor and/or deposition of solid alkyl aminobenzoate and reaction products therefrom on the reactor equipment.

Equation 2 illustrates one embodiment of the process described herein that is used to form an end-product mixture containing the aminobenzoate ester (3). In Equation 2, an alkyl aminobenzoate (1) and an alcohol reagent (2) form the reaction mixture. An auxiliary alcohol (5), having the formula $R^3OH$ wherein $R^3$ refers to an alkyl or alkylene group comprising from 1 to 14 carbon atoms and having a boiling point that is less than the boiling point of both the alkyl aminobenzoate (1) and aminobenzoate ester (3), is introduced into the reaction mixture. The auxiliary alcohol (5) reacts with both the alkyl aminobenzaote (1) and the alcohol reagent (2) thereby forming an alcohol byproduct (4). The auxilliary alcohol (5) and the alcohol by-product (4) can be easily removed from the reaction mixture using distillation, fractionation, stripping, or other means. In order to facilitate removal of the auxilliary alcohol (5) and the by-product alcohol (4) produced by reactions of the alkyl aminobenzoate (1) it may be preferable to run a portion of the reaction under partial or full vacuum.

Equation 2

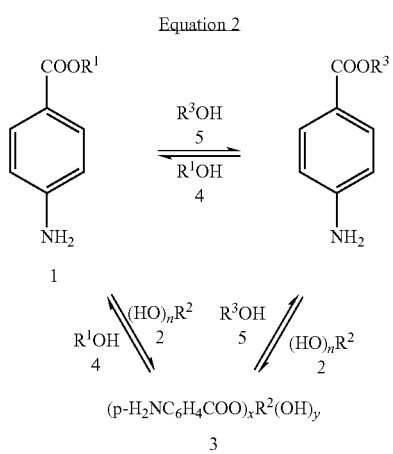

(p-H$_2$NC$_6$H$_4$COO)$_x$R$^2$(OH)$_y$
3

The reaction mixture contains at least one alkyl aminobenzoate. Suitable alkyl aminobenzoates include those having the following formula (II): NH$_2$C$_6$H$_4$COOR$^1$. In formula (II), R$^1$ is an alkyl moiety comprising from 1 to 20, or from 1 to 12, or from 1 to 4 carbon atoms which be straight-chain or branched such as, but not limited to, methyl, ethyl, propyl, butyl, hexyl, heptyl, octyl, nonyl, decyl, undecyl, dodecyl, and isomers thereof. The term "alkyl" as used herein also applies to alkyl moieties contained in other groups such as haloalkyl, alkaryl, or aralkyl. In certain embodiments, the alkyl aminobenzoate can be methyl 4-aminobenzoate, butyl 4-aminobenzoate, ethyl 4-aminobenzoate, or combinations thereof. In a preferred embodiment, the alkyl aminobenzoate is ethyl 4-aminobenzoate. The amount of alkyl aminobenzoate present in the reaction mixture may range from 0.1 to 2.0, or from 0.5 to 1.1, or from 0.8 to 1.0 equivalents per equivalent of polyol hydroxyl groups in the alcohol reagent.

In certain preferred embodiments, the alkyl aminobenzoate has from 1 to 4 carbon atoms. In these embodiments, the use of an alkyl aminobenzoate with fewer carbon atoms in the alkyl group reduces the reaction time to provide the end product mixture. For example, in embodiments where the alkyl aminobenzoate reagent is ethyl 4-aminobenzoate rather than butyl 4-aminobenzoate, the reaction time of the ethyl 4-aminobenzoate with the alcohol is substantially less than the reaction time of butyl 4-aminobenzoate with the alcohol. In these embodiments, the lower molecular weight alkyl aminobenzoates not only provide intrinsic reaction rates that are higher than the higher molecular weight alkyl 4-aminobenzoates, but also when the auxilliary alcohol is introduced into the reaction mixture to provide continuous reflux, the reaction can be run at higher temperatures, for example temperatures of 120° C. or greater, without loss of the alkyl aminobenzoate from the reaction mixture, thereby further reducing the reaction time.

The reaction mixture also contains at least one alcohol reagent. The molecular weight of the alcohol reagent may range from 60 to 10000, or from 200 to 5000, or from 500 to 2000. Exemplary alcohol reagents include oligomeric or polymeric alcohols or polyols such as, but not limited to, poly(tetrahydrofuran), poly(propylene glycol), 1,4-butanediol, and combinations thereof. Further exemplary alcohol reagents include those compounds having the following formula (III): (OH)$_n$R$^2$, where R$^2$ can be any linear or branched combination of alkyl and/or alkylene groups, which may be substituted or unsubstituted, and n is the number of attached hydroxyl groups. The term "substituted" as used herein means that the alkyl and/or alkylene groups may contain one or more other elemental atoms, such as oxygen, nitrogen, sulfur and/or other atoms besides carbon atoms. In certain embodiments, one or more of the alkyl and/or alkylene groups may be substituted with oxygen atoms. Examples of suitable R$^2$ groups may include, but not be limited to, —(CH$_2$)$_{11}$—CH$_3$, —CH$_2$—CH$_2$—CH$_2$—, —[CH$_2$—CH$_2$—CH$_2$—CH$_2$—O]$_m$—CH$_2$—CH$_2$—CH$_2$—CH$_2$—, and —[CH$_2$—CH$_2$—O]$_m$—CH$_2$—CH$_2$—, where m refers to the number of repeat units. In a preferred embodiment, the alcohol is poly(tetrahydrofuran). In the process described herein, it is preferred that the alcohol is sufficiently non-volatile to permit the preferential removal of the auxiliary alcohol and alcohol by-product. In other words, the alcohol reagent used within the reaction mixture preferentially has a boiling point that is higher than the auxiliary alcohol and alcohol by-product and one or more reagents within the reaction mixture. For example, in one embodiment the reaction mixture contains ethyl 4-aminobenzoate, poly(tetrahydrofuran) of hydroxyl number 112 mg KOH/g, and 1-butanol. In this embodiment, the polytetrahydrofuran has a vapor pressure of less than 10 mm of mercury at a temperature of 150° C., which is higher than the normal boiling point of 1-butanol or 116° C. and the normal boiling point of the alcohol by-product of the reaction between the ethyl 4-aminobenzoate and 1-butanol or ethanol which is 82° C.

In the process described herein, at least a portion of the reaction between the alkyl aminobenzoate and alcohol reagent occurs in the presence of at least one auxiliary alcohol. The auxilliary alcohol may be present within the reaction mixture itself or may be introduced before, during, and/or after the reaction of the alkyl aminobenzoate with the alcohol reagent has been initiated. In this regard, the complete alcohol charge, or a portion thereof, may be added prior to the onset of reaction, continuously during the reaction step, or a combination thereof. In preferred embodiments, the auxiliary alcohol is an alcohol having the formula R$^3$OH where R$^3$ is an alkyl or alkylene group having from 1 to 14 carbon atoms, or from 2 to 8 carbon atoms, such as, but not limited to, n-butanol, isopropanol, ethanol, n-propanol, methanol, 2-propanol, propanol, isobutanol, pentanol, isoamylalcohol, 2-ethyl-1-hexanol, 2-methyl-1-butanol and combinations thereof. Of the foregoing, it is preferred that the auxilliary alcohol itself and/or alcohol by-product of the reaction of one or more reagents within the reaction mixture and the auxilliary alcohol should be easily removed from the end product mixture without damaging the end product. In alternative embodiments, the auxilliary alcohol may be present within the end product mixture in an amount that is 5 weight percent of the end product mixture or less, or 0.5 weight percent of the end product mixture or less. The amount of the auxilliary alcohol present in the reaction mixture may range from 0.1 to 5.0, or from 0.1 to 2.0, or from 0.5 to 2.0 moles per mole of alkyl aminobenzoate. In one particular embodiment, the stoichiometric ratio of auxiliary alcohol to alkyl aminobenzoate in the reaction mixture is 1.0:1.0.

The reaction of the alkyl aminobenzoate with the alcohol reagent occurs in the presence of a catalyst that is suitable for transesterification reactions. The amount of catalyst present in the reaction mixture is that which is sufficient to facilitate the reaction between the alkyl aminobenzoate and the alcohol reagent and may range from about 0.001 to about 10 weight percent, or from about 0.001 to about 5 weight percent, or from about 0.005 to about 0.01 weight percent. Examples of suitable transesterification catalysts that can be used with the process described herein include, but are not limited to, stannous octoate, stannous oxalate, dibutyltindilaurate, dioctyltindilaurate, dibutyltindi-2-ethylhexoate, tetraisopropyl titanate, tetrabutyl titanate, tetrakis-2-ethylhexyl titanate, dibutyltindilauryl mercaptide, dibutyltindiisooctylmercapto acetate, dioctyltindilauryl mercaptide, dimethyltindilauryl mercaptide, dimethyltindiisooctylmercapto acetate, dibutyltin oxide, butyl stannoic acid, and combinations thereof.

The reaction mixture is exposed to conditions sufficient to provide an end-product mixture containing the alkyl aminobenzoate ester. In certain embodiments, the end product mixture contains as a major component an alkyl aminobenzoate ester having the following formula (I): $(NH_2C_6H_4COO)_xR^2(OH)_y$, wherein $R^2$ is a linear or branched, substituted or unsubstituted alkyl and/or alkylene group comprising from 3 to 300 carbon atoms, and x and y are each independently numbers ranging from 0 to 100 and wherein neither x nor y can be concurrently 0. In formula (I), x is the number of hydroxyl groups that are esterified and y is the number of hydroxyl groups that are not esterified. In embodiments wherein the alcohol reagent has formula (III) or $(OH)_nR^2$ the sum of the expression "x+y" in formula (I) is equal to the total number of hydroxyl units or 'n' in formula (III). The end-product mixture may contain either the pure ester (e.g., y=0 in the above formula) or a mixture of species in which the alcohol functional groups on the compound have been esterified to varying extents. In the latter embodiments, the end-product mixture may contain both partially- and fully-esterified materials $(NH_2C_6H_4COO)_x(OH)_{n-x}R^2$, such that x=1 to n or the number of hydroxyl groups on the alcohol reagent charged to the reaction mixture.

There are a number of ways that the process described herein can be conducted. In certain preferred embodiments, the reaction mixture is heated to a temperature and for a time sufficient to react the reagents contained therein and form one or more by-products of the reaction solvent and reagents contained within the reaction mixture and the end product mixture. Depending upon the reagents contained within the reaction mixture, the reaction temperature may range from 80° C. to 200° C., or from 120° C. to 200° C., or from 120° C. to 180° C. The reaction time may range from about 0 hours or instantaneous to about 100 hours, or from about 0 to about 60 hours, or from about 4 to about 48 hours. In certain embodiments, the alkyl aminobenzoate ester may be removed from the end product mixture by standard procedures such as distillation, chromatography, recrystallization, and/or titration. In other embodiments, the percentage yield of alkyl aminobenzoate ester within the end product mixture may be sufficiently high to avoid the need for additional processing steps. In this or other embodiments, the amount of unreacted materials present within the end product mixture may be sufficiently low (e.g., 5% weight percent of end product mixture or less) due to the volatility of the materials or may remain within the end product mixture because the materials are acceptable impurities within the product.

In one embodiment, the reagents (e.g., alkyl aminobenzoate, alcohol reagent, auxiliary alcohol, and transesterification catalyst) are allowed to react at appropriate temperature and pressure under conditions of total reflux for sufficient time to achieve a significant reaction of alkyl aminobenzoate with either the auxilliary alcohol, the alcohol reagent, or both. This conversion is sufficient once the concentration of alkyl aminobenzoate in the reactor is reduced to the point where its volatility is no longer an issue in terms of operability or yield. Because these reactions are typically limited by equilibrium, in this embodiment it may be necessary to use a higher level of auxilliary alcohol to achieve the desired reduction in alkyl aminobenzoate concentration. Once this depletion of the alkyl aminobenzoate is achieved, the reflux can be eliminated and both the auxilliary alcohol and the alcohol by-product can be removed as overhead condensate, in order to remove the equilibrium constraints and drive the desired reactions forward.

In certain preferred embodiments, the process is conducted using a distillation process. In these embodiments, the by-product of the reaction between the auxilliary alcohol and one or more reagents may be selectively removed while at least a portion of the auxilliary alcohol remains within the reaction mixture. For example, in embodiments where the reaction mixture contains ethyl 4-aminobenzoate and 1-butanol, the overhead vapors can be fractionated such that ethanol (the by-product of the reaction between ethyl 4-aminobenzoate and 1-butanol and/or the alcohol reagent) is preferentially removed from the reaction mixture and 1-butanol is refluxed. In these embodiments, the arrangement of the distillation equipment is preferably such that all the piping between the reactor and the column are wetted by the reflux—or are kept above 88° C. the melting point of ethyl 4-aminobenzoate—to minimize deposition of solid ethyl 4-aminobenzoate. In these embodiments, the ethanol by-product is preferentially removed initially from the reaction mixture followed by the 1-butanol auxiliary alcohol. Once the majority of the alcohol by-product has been removed by fractional distillation, the reflux can be eliminated and both the auxilliary alcohol and the residual amounts of the by-product alcohol can be taken off as overhead condensate, in order to remove the equilibrium constraints and drive the desired reactions forward. In this embodiment, the 1-butanol auxiliary alcohol condensed overhead will be sufficiently pure such that it may be reused in subsequent batches.

The teachings of the process described herein has applicability for large scale (production rates in excess of 1000 standard liters per minute), medium bench scale (production rates between 1000 to 10 standard liters per minute), small scale (production rates less than 10 standard liters per minute), and everything in between.

The process described herein may be described using certain alphabetical letters such as in the Summary of the Invention and in the Claims. This is not meant to imply chronological order. Indeed, unless otherwise specified, the method or process steps may be conducted in a variety of different orders, e.g., concurrently, sequentially, etc.

The process described herein will be illustrated in more detail with reference to the following Examples, but it should be understood that the process is not deemed to be limited thereto.

EXAMPLES

For the following examples, the gas chromatograph ("GC") analyses were carried out on a 30 m×0.25 mm×0.25 μm HP5-MS capillary column. NMR analyses for the examples were obtained on a Bruker DRX 400 FT-NMR spectrometer operated at 470.67.4 MHz ($^{19}F$), 500.29 MHz ($^1H$). Chemical shifts were referenced to the $CFCl_3$ solvent.

Comparative Example 1

Neat Laboratory Preparation of 4-aminobenzoate Diester of Poly(tetrahydrofuran) of Average Molecular Weight 1000 from Ethyl 4-aminobenzoate Ethyl 4-aminobenzoate (47.08 g) and poly(tetrahydrofuran) (147.40 g of material with hydroxyl number 112.0) were charged into a 250 mL roundbottom flask equipped with a magnetic stir bar, nitrogen sparge and a water-cooled overhead condenser and Dean-Stark trap assembly. The reactor was purged with nitrogen. Tetra(n-butoxide) titanium (IV) (0.18 g) was added and the reactor contents were heated to 165° C. at atmospheric pressure, with agitation. The reaction was maintained at 165-171° C. for 24 hours and was sampled periodically to follow the conversion of ethyl 4-aminobenzoate. After 24 hours, the reaction was shut down with a residual ethyl 4-aminobenzoate concentration of 2.8 weight percent. The final yield, accounting for the losses due to sampling, was 95% of the theoretical value. However, roughly a 1" length of the ½" glass tube leading to the Dean-Stark trap was completely bridged with needle crystals. These were dissolved in methanol and analyzed by gas chromatography, and were confirmed to be essentially pure ethyl 4-aminobenzoate.

Example 2

Laboratory Preparation of 4-aminobenzoate Diester of Poly(tetrahydrofuran) of Average Molecular Weight 1000 from Ethyl 4-aminobenzoate Using One Equivalent of 1-butanol Ethyl 4-aminobenzoate (46.94 g), poly(tetrahydrofuran) (147.5 g of material with hydroxyl number 112.0) and 1-butanol (20.91 g) were charged to a 250 mL roundbottom flask equipped with a magnetic stir bar, nitrogen sparge and a water-cooled overhead condenser and Dean-Stark trap assembly. The reactor was purged with nitrogen. Tetra(n-butoxide) titanium (IV) (0.18 g) was added and the reactor contents were heated to 150° C. at atmospheric pressure, with agitation. The reaction was maintained at 150-157° C. for 16 hours and was sampled periodically to follow the conversion of ethyl 4-aminobenzoate. At that point the reactor temperature was increased to 165-170° C. and maintained for an additional 76 hours, at which point there was 0.09 weight percent residual ethyl 4-aminobenzoate and 1.60 weight percent residual butyl 4-aminobenzoate. The final yield, accounting for the losses due to sampling, was 96% of the theoretical value. Unlike Comparative Example 1, no deposition of solids was observed in the overhead glassware.

Example 3

One-liter Laboratory Preparation of 4-aminobenzoate Diester of Poly(tetrahydrofuran) of Average Molecular Weight 1000 from Ethyl 4-aminobenzoate Using One Equivalent of 2-ethylhexanol Ethyl 4-aminobenzoate (165.2 g), poly(tetrahydrofuran) (507.3 g of material with hydroxyl number 115.2) and 2-ethylhexanol (130.3 g) were charged to a 1-liter glass kettle equipped with a direct drive impeller, nitrogen sparge, 1-foot glass distillation column with Propak random packing and a condenser and adjustable reflux splitter assembly. The reactor was purged with nitrogen and the contents were heated to reflux at 8.3 mm Hg absolute pressure, with agitation. Approximately 12 mL of distillate was taken off to ensure that the reactor contents were essentially water-free. Titanium (IV) butoxide (0.50 g) was added, the absolute pressure was lowered to 60 mm Hg and the reactor contents were reheated to reflux (around 150° C.) with agitation. The reaction was maintained at 150-170° C. for a total of 75 hours. During the final 24 hours the column was replaced with a simple pot-to-pot distillation assembly and the nitrogen purge was increased significantly to assist in bringing the residual 2-ethylhexanol over. The finished product was analyzed by gas chromatography and $^{13}C$ NMR. Both 2-ethylhexanol and 2-ethylhexyl-4-aminobenzoate were present in less than 0.1 weight percent. The final yield, accounting for the losses due to sampling, was essentially 100% of the theoretical value. No deposition of solids was observed in the overhead glassware.

Example 4

Comparative Rates of Reaction of Ethyl 4-aminobenzoate and Butyl 4-aminobenzoate with Poly(tetrahydrofuran) of Average Molecular Weight 1000

Ethyl 4-aminobenzoate (0.225 mol) and butyl 4-aminobenzoate (0.225 mol) were charged to a one-liter glass kettle equipped with a direct-drive impeller, nitrogen sparge, 1-foot glass distillation column with Propak random packing and a condenser and adjustable reflux splitter assembly. Poly (tetrahydrofuran) (228.3 g of material with hydroxyl number 115.0) and 180 mL of xylenes were added. The function of the xylenes was to maintain a reflux to keep the ethyl 4-aminobenzoate in the reactor while allowing ethanol and 1-butanol to escape. The reaction mass was heated to total reflux under vacuum (150° C. at 580 mm Hg absolute pressure) and a small amount of material was taken overhead to remove any trace water from the system. Titanium (IV) butoxide (0.45 g) was then added and total reflux was restored. Once steady-state was achieved at atmospheric pressure and a reactor temperature of 156° C., a very slow removal of distillate was initiated to remove the alcohols as they were formed. It was acknowledged that small amounts of xylenes would be lost as well. The reactor temperature was maintained at 160-175° C. by gradually decreasing the absolute reactor pressure. Samples were withdrawn periodically and analyzed for ethyl 4-aminobenzoate and butyl 4-aminobenzoate content by gas chromatography. The data are plotted in FIG. 1 as moles of each component (in arbitrary units) versus time in a semi-log fashion. These results show that the rate of reaction of ethyl 4-aminobenzoate with the poly(tetrahydrofuran) is roughly twice as fast as that of butyl 4-aminobenzoate. This verifies the benefit of using ethyl 4-aminobenzoate rather than butyl 4-aminobenzoate in shortening overall reaction time, in addition to the raw material cost advantage.

Example 5

Commercial Scale Preparation of 4-aminobenzoate Diester of Poly(tetrahydrofuran) of Average Molecular Weight 1000 from Ethyl 4-aminobenzoate Using One Equivalent of 1-butanol Ethyl 4-aminobenzoate (4960 pounds), poly(tetrahydrofuran) (16020 pounds of material with hydroxyl number 109.4) and 1-butanol (2244 pounds) were charged to a commercial jacketed reactor, with cooling coils, three pitched-blade impellers, and an overhead distillation column and condenser. An analysis of the reactor contents showed less than 0.05% water. Titanium (IV) butoxide (10 pounds) was added and the reactor contents were heated to 150° C. at roughly 610 mm Hg absolute pressure, with agitation. Total reflux was maintained until the overheads were enriched in ethanol as indicated by the overhead temperature falling below 80° C. At that point distillate take-off was initiated. Approximately three hours later it began to be necessary to begin lowering the absolute pressure to keep the reactor temperature below 170° C., and eventually the steam rate to the jacket needed to be throttled as well. Once distillate stopped coming over, the reactor was held at 160-170° C. with nitrogen sparge and agitation to complete the reaction. After a total of 27 hours from the time distillate take-off was initiated the residual butyl 4-aminobenzoate level was 2.0 weight percent, and after 33 hours it was 1.2 weight percent. At that point the reactor contents were cooled and packaged. The final yield was 97% of the theoretical value. No deposition of solids was observed in the overhead piping or distillation equipment.

Figure 2:
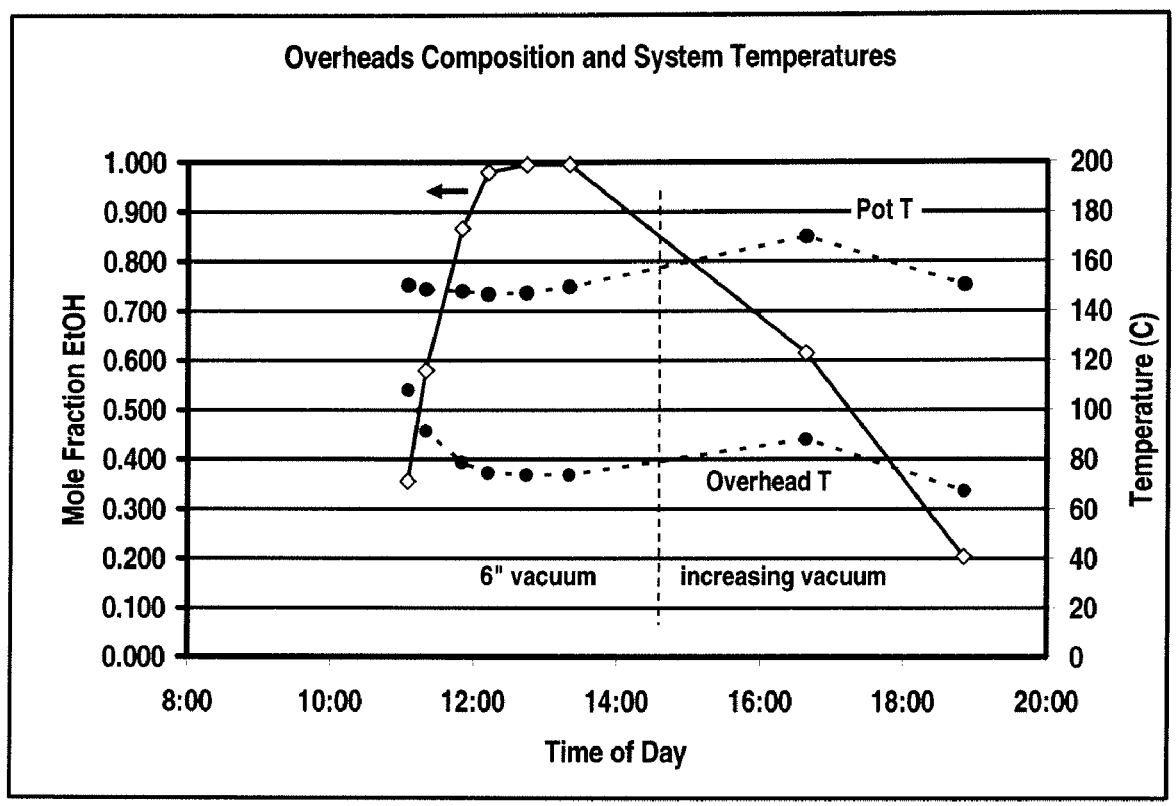
FIG. 2 provides the results of gas chromatograph ("GC") analysis of various samples of distallate obtained in Example 5.

A number of samples were withdrawn from the reflux line, providing a measurement of the composition of the distillate at that time and the compositions and temperatures of these samples are indicated in FIG. 2 by white diamonds and black circles, respectively. The examples illustrates that the ethanol by-product can be selectively removed from the reaction of ethyl 4-aminobenzoate either with 1-butanol or with poly (tetrahydrofuran), while retaining the bulk of the 1-butanol in the reactor.

Example 6

Laboratory Preparation of 4-aminobenzoate Diester of Poly(propylene glycol) of Average Molecular Weight 2000 from Ethyl 4-aminobenzoate Using One Equivalent of 1-butanol Ethyl 4-aminobenzoate (82.6 g), poly(propylene glycol) (536.8 g of material with hydroxyl number 55.39) and 1-butanol (55.6 g) were charged to a 1-liter glass kettle equipped with a direct drive impeller, nitrogen sparge, 1-foot glass distillation column with Propak random packing and a condenser and adjustable reflux splitter assembly. The reactor was purged with nitrogen and the contents were heated to reflux at 300 mm Hg absolute pressure, with agitation. Approximately 12 g of distillate was taken off to ensure that the reactor contents were essentially water-free. Titanium (IV) butoxide (1.05 g) was added, the absolute pressure was lowered to 300 mm Hg and the reactor contents were reheated to reflux (around 170° C.) with agitation. The absolute pressure was gradually reduced to maintain boil-up and reflux. The reaction was maintained at 170-175° C. for a total of 28.6 hours; for roughly the last 25 hours the absolute pressure was less than 10 mm Hg. The finished product was analyzed by gas chromatography and $^{13}C$ NMR. A 95.5% conversion of PABAs to product esters was measured and the identity of the monoester and diester products was confirmed. No deposition of solids was observed in the overhead glassware.

The invention claimed is:

1. A process for preparing an end-product mixture comprising an aminobenzoate ester comprising the following formula (I) $(NH_2C_6H_4COO)_xR^2(OH)_y$ wherein $R^2$ is a linear or branched, substituted or unsubstituted alkyl and/or alkylene group having from 3 to 300 carbon atoms and wherein x and y are each independently a number ranging from 0 to 100 provided that neither x nor y can be zero concurrently, the process comprising the steps of:
   (a) providing a reaction mixture comprising an alkyl aminobenzoate comprising the following formula (II) $NH_2C_6H_4COOR^1$ where $R^1$ is an alkyl group having from 1 to 20 carbon atoms, an alcohol reagent comprising the following formula $(HO)_nR^2$ wherein n is a sum of the expression "x+y" and an auxiliary alcohol wherein the auxiliary alcohol has a vapor pressure that is greater than a vapor pressure of the alkyl aminobenzoate and the aminobenzoate ester wherein at least a portion of the auxiliary alcohol within the reaction mixture reacts to provide an alcohol by-product and wherein the alcohol by-product has a boiling point that is less than a boiling point of the auxiliary alcohol; and
   (b) exposing the reaction mixture to conditions effective to provide an end-product mixture comprising the aminobenzoate ester.

2. The process of claim 1 wherein a stoichiometric ratio of alkyl aminobenzoate to alcohol functional groups in the reaction mixture is less than 2:1.

3. The process of claim 1 wherein the amount of auxiliary alcohol to alkyl aminobenzoate present in the reaction mixture ranges from 0.1 to 5.0 moles per mole of alkyl aminobenzoate.

4. The process of claim 1 wherein a stoichiometric ratio of auxiliary alcohol to alkyl aminobenzoate in the reaction mixture is 1.0:1.0.

5. The process of claim 1 wherein $R^1$ comprises from 1 to 12 carbon atoms.

6. The process of claim 5 wherein $R^1$ comprises from 1 to 4 carbon atoms.

7. The process of claim 1 wherein the alkyl aminobenzoate is ethyl 4-aminobenzoate.

8. The process of claim 4 wherein the auxiliary alcohol is 1-butanol.

9. A process for making an aminobenzoate ester comprising the steps of:
   (a) providing a reaction mixture comprising an alkyl aminobenzoate and an alcohol wherein at least a portion of the alcohol reagent reacts with the alkyl aminobenzoate to provide an alcohol by-product reagent;
   (b) introducing an auxiliary alcohol to the reaction mixture wherein the auxiliary alcohol has a boiling point that is less than a boiling point of the alkyl aminobenzoate and a boiling point of the aminobenzoate ester and higher than a boiling point of the alcohol by-product; and
   (c) heating the reaction mixture to a temperature of 120° C. or greater for a time sufficient to produce an end-product mixture comprising the aminobenzoate ester.

10. The process of claim 9 wherein step (b) is conducted during at least a portion of step (a).

11. The process of claim 10 wherein step (b) is conducting during at least a portion of step (c).

12. The process of claim 9 wherein step (b) is conducted during at least a portion of step (c).

13. The process of claim 9 wherein step (c) is conducted using a distillation column.

14. The process of claim 13 further comprising: (d) removing the alcohol byproduct from step (c).

15. A process for making an aminobenzoate ester of a polymerized alcohol comprising the steps of:
   (a) providing a reaction mixture comprising an alkyl aminobenzoate, an alcohol reagent, and a transesterification catalyst;
   (b) introducing an auxiliary alcohol to the reaction mixture wherein at least a portion of the auxiliary alcohol within the reaction mixture reacts to provide an alcohol by-product and wherein the alcohol by-product has a vapor pressure that is higher than a vapor pressure of the auxiliary alcohol; and
   (c) exposing the reaction mixture to conditions effective to provide an end-product mixture comprising the aminobenzoate ester.

16. The process of claim 15 wherein further comprising (d) removing at least a portion of the alcohol by-product from the reaction mixture wherein at least a portion of the auxiliary alcohol remains within the reaction mixture.

17. The process of claim 16 wherein removing step (d) is conducted using a distillation column.

* * * * *

UNITED STATES PATENT AND TRADEMARK OFFICE
CERTIFICATE OF CORRECTION

PATENT NO. : 7,547,798 B2
APPLICATION NO. : 11/829418
DATED : June 16, 2009
INVENTOR(S) : Andrew Wilson Wang and George Ernest Grossmann It is certified that error appears in the above-identified patent and that said Letters Patent is hereby corrected as shown below:

Column 12, Line 25

In claim 9 (a) insert -- reagent -- after the word alcohol

Column 12, Line 27

In claim 9 (a) delete "reagent"

Signed and Sealed this

Twenty-eighth Day of July, 2009

JOHN DOLL
*Acting Director of the United States Patent and Trademark Office*